United States Patent
Haesslin et al.

(10) Patent No.: US 6,849,575 B2
(45) Date of Patent: Feb. 1, 2005

(54) HERBICIDAL COMPOSITION

(75) Inventors: Hans Walter Haesslin, Muenchwilen (CH); Marlène Torrent, Greensboro, NC (US); Christian Schlatter, Greensboro, NC (US)

(73) Assignee: Syngenta Crop. Protection, Inc., Greensboro, NC (US)

( * ) Notice: Subject to any disclaimer, the term of this patent is extended or adjusted under 35 U.S.C. 154(b) by 0 days.

(21) Appl. No.: 10/468,548

(22) PCT Filed: Feb. 25, 2002

(86) PCT No.: PCT/EP02/01963

§ 371 (c)(1),
(2), (4) Date: Aug. 20, 2003

(87) PCT Pub. No.: WO02/067682

PCT Pub. Date: Sep. 6, 2002

(65) Prior Publication Data

US 2004/0082476 A1 Apr. 29, 2004

(30) Foreign Application Priority Data

Feb. 26, 2001 (CH) .................................... 2001 0348/01

(51) Int. Cl.$^7$ .................... A01N 25/02; A01N 25/32; A01N 43/40
(52) U.S. Cl. .................... 504/105; 504/258; 504/363
(58) Field of Search ............................... 504/105, 258, 504/363

(56) References Cited

U.S. PATENT DOCUMENTS

| | | | | |
|---|---|---|---|---|
| 4,713,109 A | * | 12/1987 | Schurter et al. | ............. 504/258 |
| 5,674,514 A | | 10/1997 | Haesslin | ..................... 424/405 |

FOREIGN PATENT DOCUMENTS

| | | |
|---|---|---|
| EP | 0 533 057 | 3/1993 |
| WO | 01 10210 | 2/2001 |

OTHER PUBLICATIONS

Hopkins, William L. Global Herbicide Directory, 1st Ed. Ag Chem Information Services. "TOPIK". p. 32. 1994.*

* cited by examiner

*Primary Examiner*—S. Mark Clardy
(74) *Attorney, Agent, or Firm*—Rose M. Allen

(57) ABSTRACT

A herbicidal composition in the form of a two-phase aqueous emulsion which comprises,
  a) as organic phase, a solution of a herbicidally effective amount of the compound 2-(4-(3-chloro-5-fluoro-2-pyridyloxy)-phenoxy-propionic acid propargyl ester in a hydrophobic solvent and a substantially water-insoluble and hydrolysis-stable oil phase stabiliser and,
  b) as aqueous phase, a solution of at least one surface-active compound and/or dispersing agent and a pH buffer in water.

4 Claims, No Drawings

HERBICIDAL COMPOSITION

The present invention relates to a herbicidal composition in the form of an aqueous emulsion which comprises, as herbicidally effective compound, 2-(4-(3-chloro-5-fluoro-2-pyridyloxy)-phenoxy-propionic acid propargyl ester, and to the use of that composition in controlling weeds in crops of useful plants.

2-(4-(3-Chloro-5-fluoro-2-pyridyloxy)-phenoxy-propionic acid propargyl ester has herbicidal activity, especially in crops of cereals, rice and soybeans; it is known by the name clodinafop-propargyl and is described, for example, in U.S. Pat. No. 4,713,109.

Clodinafop-propargyl is preferably used together with the safener 2-(5-chloroquinolin-8-yloxy)-1-methylhexyl ester, which is known by the name cloquintocet-mexyl and is described, for example, in U.S. Pat. No. 4,881,966. Both compounds are commercially available in the form of an emulsifiable concentrate (EC).

Aqueous emulsions for the formulation of pesticides are known per se and are described, for example, in U.S. Pat. No. 5,674,514. The problem solved in U.S. Pat. No. 5,674,514 was to provide an aqueous emulsion for the purpose of improving the storage stability of certain pesticides. U.S. Pat. No. 5,674,514 contains no reference whatsoever to changes in the biological activity of pesticides formulated in that manner.

It has now been found, surprisingly, that the herbicidal activity of clodinafop-propargyl can be considerably increased when that compound is applied in the form of a particular aqueous emulsion.

The present invention accordingly relates to a herbicidal composition in the form of a two-phase aqueous emulsion which comprises a), as organic phase, a solution of a herbicidally effective amount of the compound 2-(4-(3-chloro-5-fluoro-2-pyridyloxy)-phenoxy-propionic acid propargyl ester in a hydrophobic solvent and a substantially water-insoluble and hydrolysis-stable oil phase stabiliser and b), as aqueous phase, a solution of at least one surface-active compound and/or dispersing agent and a pH buffer in water.

Preferred compositions according to the invention additionally comprise an amount, effective for antagonism of the herbicide, of 2-(5-chloroquinolin-8-yloxy)-1-methylhexyl ester, its free acid or a salt thereof of formula

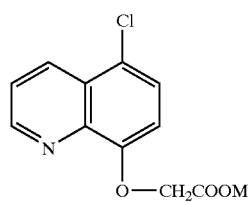

(I)

wherein M is a mono-, bi- or tri-valent metal, ammonium, $N(R)_4$ or $HN(R)_3$, wherein the substituents R are identical to or different from one another and are $C_1$–$C_{16}$alkyl or $C_1$–$C_{16}$-hydroxyalkyl, or M is $S(R_1)_3$ or $P(R_1)_4$, wherein the substituents $R_1$ are identical to or different from one another and are $C_1$–$C_{20}$alkyl, $C_2$–$C_{20}$alkenyl, $C_2$–$C_{20}$alkynyl, aryl substituted by $C_1$–$C_{20}$alkyl, $C_2$–$C_{20}$alkenyl or by $C_2$–$C_{20}$alkynyl or heteroaryl substituted by $C_1$–$C_{20}$alkyl, $C_2$–$C_{20}$-alkenyl or by $C_2$–$C_{20}$alkynyl, or 2 substituents $R_1$ together with the sulfur or phosphorus atom to which they are bonded form a 5- or 6-membered ring.

The metal atoms M that may be present in formula I are preferably those of alkali and alkaline earth metals, especially sodium, potassium, calcium, magnesium and also, especially, aluminium and iron as preferred representatives of trivalent metals. Among the alkyl and hydroxyalkyl substituents R, preference is given to those having from 12 to 16 carbon atoms and also to those having from 1 to 4 carbon atoms. The groups $N(R)_4$ and $HN(R)_3$ especially contain one long-chain and 2 or 3 short-chain alkyl group(s), for example hexadecyl-triethylammonium, tetradecyl-triethylammonium, dodecyltriethylammonium and dodecyl-ethyl-dimethylammonium, and also tetradodecylammonium. Preferred alkyl groups $R_1$ contain from 1 to 12, especially from 1 to 6, carbon atoms. The alkyl groups R and $R_1$ may be further substituted, for example by halogen, alkoxy or by haloalkoxy, in both cases preferably containing from 1 to 4 carbon atoms. Preferred alkenyl and alkynyl groups $R_1$ contain from 2 to 12 carbon atoms. They may contain more than one unsaturated bond and may be substituted by halogen, alkoxy or by haloalkoxy, in both cases preferably containing from 1 to 4 carbon atoms. Suitable examples of aryl groups $R_1$ include phenyl, naphthyl, tetrahydronaphthyl, indanyl and indenyl, phenyl being preferred. Those groups may be substituted by the aforementioned alkyl, alkenyl and alkynyl groups. As heteroaryl groups $R_1$ there may be mentioned preferably 5- and 6-membered rings containing especially nitrogen and/or oxygen atoms, for example pyridyl, pyrimidinyl, triazinyl, thienyl, thiazolyl, pyrazolyl, imidazolyl, piperidyl, dioxolanyl, morpholinyl and tetrahydrofuryl. Those heterocycles may also be further substituted by the aforementioned alkyl, alkenyl and alkynyl groups. In each case, 2 substituents $R_1$ together with the sulfur or phosphorus atom to which they are bonded may form a ring, in which case preference is given to 5- or 6-membered rings that are saturated. Sulfonium and phosphonium cations suitable for use according to the invention are described, for example, in WO 00/44227.

Preferred salts of 2-(5-chloroquinolin-8-yloxy)-1-methylhexyl ester comprise a compound of formula I wherein M is sodium, potassium or tri(hydroxyethylene) ammonium.

In a further group of preferred salts of 2-(5-chloroquinolin-8-yloxy)-1-methylhexyl ester, M in formula I is calcium, magnesium, aluminium, iron, trimethylsulfonium, triphenylsulfonium, tetraphenylphosphonium, triphenyl-methylphosphonium, triphenyl-benzylphosphonium, $C_{12}$–$C_{16}$alkyl-trimethylammonium, $C_{12}$–$C_{16}$alkyl-triethylammonium, tetradodecylammonium or dodecyl-ethyl-dimethylammonium.

The salts of formula I can be prepared by conventional methods, for example by reacting 2-(5-chloroquinolin-8-yloxy)-1-methylhexyl ester with an equimolar amount of a metal hydroxide in alcoholic solution at room temperature.

The salts set out in the following Table can be prepared in that manner:

TABLE 1

Compounds of formula I:

| Compound no. | M | M.p. (° C.) |
|---|---|---|
| 1.01 | Na | >250 |
| 1.02 | K | >265 |
| 1.03 | Ca | |
| 1.04 | Mg | |
| 1.05 | $NH_4$ | 227–228 |

TABLE 1-continued

Compounds of formula I:

| Compound no. | M | M.p. (° C.) |
|---|---|---|
| 1.06 | NH(CH$_2$CH$_2$OH)$_3$ | 132–152 |
| 1.07 | N(C$_{12}$H$_{25}$)$_4$ | |
| 1.08 | N(C$_{12}$H$_{25}$)(C$_2$H$_5$)(CH$_3$)$_2$ | |
| 1.09 | N(C$_{12}$H$_{25}$)(CH$_3$)$_3$ | |
| 1.10 | N(C$_{12}$H$_{25}$)(C$_2$H$_5$)$_3$ | |
| 1.11 | Al | |
| 1.12 | Fe | |
| 1.13 | H | 232–233 |
| 1.14 | S(CH$_3$)$_3$ | |
| 1.15 | S(C$_6$H$_5$)$_3$ | |
| 1.16 | P(C$_6$H$_5$)$_4$ | |
| 1.17 | P(C$_6$H$_5$)$_3$CH$_3$ | |
| 1.18 | P(C$_6$H$_5$)$_3$CH$_2$C$_6$H$_5$ | |

The compositions according to the invention may comprise one or more herbicides in addition to clodinafop-propargyl. Such herbicides are preferably selected from the groups of the sulfonylureas, sulfonamides, imidazolinones, carbazones, aryloxyphenoxypropionates, cyclohexanediones, arylcarboxylic acids and aryloxycarboxylic acids. Depending on their solubility, those herbicides may be dissolved either in the continuous aqueous phase or in the discontinuous oil phase or may be suspended in either of the two phases.

As herbicides that are especially suitable for use in the composition according to the invention mention may be made of, especially, sulfonylureas, preferably triasulfuron, tribenuron, metsulfuron, thifensulfuron, flupyrsulfuron, iodosulfuron, rimsulfuron, nicosulfuron, cinosulfuron, bensulfuron, trifloxysulfuron and analogues, and also sulfonamides, preferably flumetsulam, metosulam, chloransulam, floransulam and analogues, and imidazolinones, preferably imazethabenz, imazethapyr, imazaquin, imazamox and analogues, and also carbazones, preferably flucarbazone, propoxycarbazine, amicarbazone and analogues, and also aryloxyphenoxypropionates, preferably fenoxaprop, diclofop, propaquizafop, quizalofop, fluazifop, cyhalofop, haloxyfop and analogues, and also cyclohexanediones, preferably sethoxydim, clethodim, tralkoxydim and analogues, and arylcarboxylic acids, preferably dicamba and clopyralid, and also aryloxycarboxylic acids, preferably 2,4-D, mecoprop, fluroxypyr and analogues.

It has also been found, surprisingly, that clodinafop-propargyl and cloquintocet-mexyl are chemically especially stable in the aqueous emulsions according to the invention when the aqueous phase comprises a pH buffer system. Suitable pH buffer systems in the context of the present invention are those mixtures of acids and salts that are capable of stabilising a pH of from 4 to 6, especially acetic acid/sodium acetate, phosphoric acid/sodium phosphate or citric acid/citrate, preferably phosphoric acid/sodium phosphate or citric acid/citrate. The aqueous phase of the compositions according to the invention are preferably adjusted to a pH of 4 with phosphoric acid/sodium phosphate or citric acid/citrate.

The pH buffer is used in an amount of from 0.1 to 1 mol, preferably from 0.2 to 0.7 mol, especially 0.5 mol, based on the aqueous phase.

In the context of the present invention, any solvent that is substantially insoluble in water is suitable as the hydrophobic solvent, for example aromatic solvents selected from the classes of the toluenes, xylenes, alkylbenzenes and alkylnaphthalenes, and also saturated and unsaturated hydrocarbons, aryl-alkyl ketones, esters, fatty acid methyl esters, rapeseed oil C$_1$–C$_6$alkyl esters, especially rapeseed oil methyl ester and rapeseed oil ethyl ester, esters of acetic acid or benzoic acid, amides of alkanecarboxylic acids, linear or cyclic acetates, alkylpyrrolidones, alkylcaprolactones and also alkyl carbonates or mixtures of those solvents. The solvent is preferably used in an amount of from 10 to 60% by weight, based on the complete formulation of the aqueous emulsion.

It has been found, moreover, that the chemical stability of the compositions according to the invention can be further increased when a hydrophobic solvent preferably of especially high polarity is used in the organic phase. In the context of the present invention, solvents of high polarity are to be understood as solvents having a dipole moment of at least $4 \times 10^{-30}$ Cm (coulomb×m). The hydrophobic solvents used in the composition according to the invention preferably have a dipole moment of at least $5 \times 10^{-30}$ Cm.

Especially preferred solvents are Exxate 700 (mixture of aliphatic acetic acid C$_6$–C$_8$ esters, Esso Switzerland), benzyl acetate, isobornyl acetate, benzoic acid methyl ester or Solvesso 200 (high-aromatic-content hydrocarbon mixture, manufacturer: Exxon Chemicals).

Oil phase stabilisers that are especially suitable for the composition according to the invention include the following polymers, copolymers and oligomers or mixtures thereof, selected from the classes of the polystyrenes, water-insoluble poly(n-alkylene) glycols wherein n>2, polypropylene glycols, polyvinyl acetates and polyvinyl acetate-co-polyethylenes.

Preferred oil phase stabilisers are:
1) Polymers of monoolefins and diolefins, for example polypropylene, polyisobutylene, polybut-1-ene, polymethylpent-1-ene, polyisoprene or polybutadiene and also polymers of cyclo-olefins, for example of cyclopentene or norbornene, polyethylene (which may optionally be cross-linked), for example high density polyethylene (HDPE), low density polyethylene (LDPE) and linear low density polyethylene (LLDPE).
2) Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).
3) Copolymers of monoolefins and diolefins with one another or with other vinyl monomers, for example ethylene/propylene copolymers, linear low density polyethylene (LLDPE) and mixtures thereof with low density polyethylene (LDPE), propylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another and with polymers mentioned under 1), for example polypropylene/ethylene-propylene copolymers, LDPE/EVA, LDPE/EAA, LLDPE/EVA and LLDPE/EAA.
3a) Hydrocarbon resins (for example C$_5$–C$_9$) including hydrogenated modifications thereof.
4) Polystyrene, poly(p-methylstyrene), poly(α-methylstyrene).
5) Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/maleic acid anhydride, styrene/acrylonitrile/methyl acrylate; mixtures consisting of styrene copolymers and another polymer, for example a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6) Graft copolymers of styrene or α-methylstyrene, for example styrene on polybutadiene, styrene on polybutadiene/styrene or polybutadiene/acrylonitrile; styrene and acrylonitrile (or methacrylonitrile) on polybutadiene; styrene and maleic acid anhydride or maleinimide on polybutadiene; styrene, acrylonitrile and maleic acid anhydride or maleinimide on polybutadiene; styrene, acrylonitrile and methyl methacrylate on polybutadiene, styrene and alkyl acrylate or methacrylate on polybutadiene, styrene and acrylonitrile on ethylene/propylene/diene terpolymer, styrene and acrylonitrile on polyalkyl acrylates or polyalkyl methacrylates, styrene and acrylonitrile on acrylate/butadiene copolymers, and mixtures thereof with the copolymers mentioned under 5), for example copolymer mixtures known under the designations ABS, MBS, ASA or AES.

7) Halogenated polymers, for example polychloroprene, chlorinated rubbers, chlorinated or sulfonated polyethylenes, copolymers of ethylene and chlorinated ethylene, epichlorohydrin homo- and co-polymers, preferably polymers of halogenated vinyl compounds, for example polyvinyl chloride, polyvinylidene chloride, polyvinyl fluoride, polyvinylidene fluoride and copolymers thereof, for example vinyl chloride/vinylidene chloride, vinyl chloride/vinyl acetate or vinylidene chloride/vinyl acetate copolymers.

8) Polymer derivatives of α,β-unsaturated acids and derivatives thereof, such as polyacrylates and polymethacrylates, polyacrylamides and polyacrylonitriles.

9) Copolymers of the monomers mentioned under 8) with one another or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

10) Polymers derived from unsaturated alcohols and amines or their acyl and acetal derivatives, for example polyvinyl acetate, polyvinyl stearate, polyvinyl benzoate, polyvinyl maleate, polyvinyl butyrate, polyallyl phthalate or polyallylmelamine; and copolymers thereof with the olefins mentioned under 1).

11) Homopolymers and copolymers of cyclic ethers, for example polyalkylene glycols, polypropylene oxides or copolymers thereof with bisglycidyl ethers.

12) Polyacetals such as polyoxymethylene and polyoxymethylenes which contain ethylene oxides as comonomer; polyacetals modified with thermoplastic polyurethanes, acrylates or MBS.

13) Polyphenylene oxides and sulfides.

14) Polyurethanes derived from polyethers, polyesters and polybutadienes which have terminal hydroxyl groups on the one hand and aliphatic or aromatic polyisocyanates on the other hand.

15) Polyamides and copolyamides derived from diamines, dicarboxylic acids and from aminocarboxylic acids of the corresponding lactams, for example polyamide 4, polyamide 6, polyamide 6/6, 6/10, 6/9, 6/12 and 4/6, polyamide 11, polyamide 12, aromatic polyamides that are obtained, by means of condensation, from m-xylene, diamine and adipic acid; polyamides that are obtained from hexamethylenediamine and isophthalic and/or terephthalic acid, with or without an elastomer as modifier, for example poly-2,4,4-trimethylhexamethylene terephthalamide or poly-m-phenylene isophthalamide; block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol; and also polyamides or copolyamides modified with EPDM or ABS, and polyamides condensed during reaction (RIM polyamide systems).

16) Polyureas, polyimides and polyamide imides and polybenzimidazoles.

17) Polyesters derived from dicarboxylic acids and diols and/or from hydroxycarboxylic acids and lactones thereof, for example polyethylene terephthalate, polybutylene terephthalate, poly-1,4-dimethylolcyclohexane terephthalate, polyhydroxybenzoates, and also block copolyether esters derived from polyethers having terminal hydroxyl groups; and also poly-esters modified with polycarbonates or MBS.

17a) Polyesters derived from aliphatic dicarboxylic acids and diols and/or oligo ethers and having the general formula

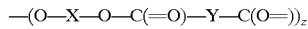

wherein
X=—(CH$_2$)$_n$— wherein n=2 to 12 or
X=[—(CH$_2$)$_n$—O—(CH$_2$)$_n$—]$_r$ wherein n=2 to 4 and r=2 to 10,
Y=—(CH$_2$)$_m$— wherein m=0 to 12,
and z=5 to 100
and copolymers thereof.

18) Polycarbonates and polyester carbonates.

19) Polysulfones, polyether sulfones and polyether ketones.

20) Polyethers of diglycidyl compounds, including diglycidyl ethers and diols, for example of diglycidyl ether of bisphenol A, and bisphenol A.

21) Natural polymers, such as rubber, and chemically modified homologous derivatives of natural polymers, for example cellulose acetates, cellulose propionates and cellulose butyrates, or cellulose ethers, for example methyl cellulose (degree of substitution >2.5); and also resins and derivatives thereof.

22) Mixtures of the afore-mentioned polymers, for example PP/EPDM, polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA6.6 and copolymers, PA/HDPE, PA/PP or PA/PPO.

23) Mineral oils, fatty acid alkyl esters or rapeseed oil C$_1$–C$_6$alkyl esters, in which case preference is given to rapeseed oil methyl ester and rapeseed oil ethyl ester.

Examples of polymers that are commercially available and especially suitable for the composition according to the invention include COETHYLENE® SB 0425 and COETHYLENE® SL (polystyrenes, Plast Labor); HOSTAFLEX® CM 13 (polyvinyl chloride/vinyl acetate copolymer); ESTERGUM® 8 D and 10 D (colophony glycerol ester); HOSTALITH® 3067 (polyvinyl chloride); HOSTYREN® 2000, 5000 and 7000 (polystyrenes); solid acrylic resins such as PLEXIGUM® N 80 (polyethyl acrylate) and M 825 (polymethyl methacrylate); polyvinyl acetate copolymers such as MOWILITH® 20 and 50 having molecular weights of 35 000 and 260 000 daltons, respectively; colophony derivatives NEOLYN® 20 and 35 D; polytetrahydrofurans; polypropylene glycols such as polyglycol T01/60 (Hoechst AG), polyvinyl acetate, Edenor ME SU (rapeseed oil methyl ester, Henkel KGAA) and also Mowilith 20 (polyvinyl acetate, Harco).

The molecular weight of the polymer of the oil phase stabilisers that are suitable for the composition according to the invention, determined, for example, by light-scattering measurements or by measurement of the osmotic pressure, can be up to 1 000 000 and is usually from 1000 to 1 000 000 daltons, preferably from 1000 to 100 000 daltons. In the case of compounds that are extremely hydrophobic and therefore of extremely low solubility in water, for example alkanes and fatty acid alkyl esters, the MW can also be less than 1000.

The oil phase stabilisers are used in the composition according to the invention in a concentration of from 0.5 to 10% by weight, preferably from 1 to 5% by weight, based on the complete formulation. In the case of compounds that are extremely hydrophobic and therefore of extremely low solubility in water, for example alkanes and fatty acid alkyl esters, and that have a low molecular weight, the concentration of the oil phase stabilisers can be up to 25%.

Surface-active substances and dispersing agents that are suitable for the present composition according to the invention include tristyrylphenol ethoxylates, for example Sopro-phor TS-10 (Rhone Poulenc S. A.) or BSU (Rhodia Geron-azzo Spa), EO/PO/EO block copolymers, for example Pluronic F-108, Pluronic F-38, Pluronic P-105 (BASF Wyandotte Corp.) and/or sodium salts of sulfonated naphthalenesulfonic acid-formaldehyde condensation products, for example Morwet D-425 (Witco Chem. Corp.) or Orotan SN (Rohm & Haas, France S. A.), lignosulfonates, PO/EO butanol copolymers, for example Atlox G-5000, block copolymers of polyhydroxystearic acid and polyalkylene glycols, for example Atlox 4912 or 4914 (American Hoechst), or partially hydrolysed or fully hydrolysed polyvinyl acetate, for example Mowiol 18-88 or Mowiol 4-88 (Hoechst AG).

The dispersing agents are preferably used in an amount of from 0.5 to 5% by weight, especially from 1 to 2% by weight, based on the complete formulation.

The formulations in accordance with the invention may additionally comprise thickeners for the continuous aqueous phase. Any thickener generally customary in formulation technology and capable of increasing the viscosity of the aqueous emulsions according to the invention is suitable, for example xanthan gum, clays or polyethylene glycols. The thickeners are preferably used in a concentration of from 0.03 to 1%, based on the complete formulation of the aqueous emulsion.

In addition, there may also be added to the formulations according to the invention substances that lower the melting point of the emulsions, that is to say that prevent the formulation from freezing at low temperatures (anti-freezing agents). Such substances are usually water-soluble salts that are suitable for lowering the freezing point of the aqueous phase of the emulsion according to the invention, for example sodium chloride, potassium chloride, ammonium chloride, ammonium nitrate and sodium nitrate and mixtures thereof. Also suitable are water-soluble glycols, for example ethylene glycol, propylene glycol, diethylene glycol, glycerol and mixtures thereof. The salts and the glycols are, in each case, preferably used in a concentration of from 0.5 to 10% by weight, based on the complete formulation of the emulsion.

The emulsions according to the invention may additionally comprise, as adjuvants, preservatives that inhibit the growth of micro-organisms such as bacteria and fungi, for example Proxel GXL (benzisothiazolin-3-one, Avecia Inc.) or formaldehyde. Such adjuvants can be used in an amount of from 0.1 to 0.5% by weight of the complete formulation.

Preparation of the emulsions according to the invention is substantially carried out using the methods described in U.S. Pat. No. 5,674,514. The organic phase can be prepared, for example, by dissolving clodinafop-propargyl, optionally together with cloquintocet-mexyl, in a hydrophobic solvent, subsequently adding the water-insoluble oil phase stabiliser and then, where appropriate, heating.

The aqueous phase is prepared by dissolving a surface-active substance and/or a dispersing agent in water, where appropriate adding substances that lower the freezing point.

The organic phase is then emulsified in the aqueous phase by means of a suitable stirrer, for example a YSTRAL® X 40/32 emulsifier, having stirring speeds of from 3000 to 6000 rpm. Depending on the formulation used and the speed, an emulsion is obtained having particle sizes in the preferred range of 1–10 micrometres. Thickeners and/or preservatives may, where appropriate, be added to the formulation before or after the emulsification step.

Whereas commercial products will preferably be formulated as concentrates, the end user will normally employ formulations diluted with water.

Preferred herbicidal compositions according to the invention have the following general compositions (all figures in % by weight, based on the complete formulation):

Oil Phase:

| |
|---|
| 5–25% clodinafop-propargyl |
| 1–6% cloquintocet-mexyl |
| 10–60% solvent |
| 1–5% oil phase stabiliser |

Aqueous Phase:

| |
|---|
| 0.05–1% thickener |
| 3–8% anti-freeze |
| 1–5% surfactants |
| 0.1–0.5% biocide |
| reminder water (buffered) |

PREPARATION EXAMPLES

Example P1

Preparation of a Herbicidal Composition Containing 100 g of Clodinafop-propargyl a) Preparation of the Thickeners 4 g of Proxel GXL are dissolved in 1946 g of water. Then, with mechanical stirring, 50 g of Biopolymer AG are added and stirring is carried out for 15 minutes until homogeneity is achieved.

b) Preparation of the Buffer Solution 11.5 g of $Na_3PO_4 \cdot 12H_2O$ and 9.0 g of $H_3PO_4$ (75%) are dissolved in 1000 ml of water and the pH is adjusted to 4 (using $Na_3PO_4 \cdot 12H_2O$ or $H_3PO_4$).

c) Preparation of the Oil Phase

In a 500 ml glass beaker, at a temperature of 20° C., 100 g of clodinafop-propargyl and 25 g of cloquintocet-mexyl are dissolved, with stirring, in 250 ml of Solvesso 200. 20 g of polystyrene are then added, and heating to a temperature of 65–70° C. is carried out. After dissolution of the ingredients is complete, the mixture is left to cool to a temperature of 20° C.

d) Preparation of the Aqueous Phase

In a 1500 ml glass beaker, at a temperature of 20° C., 10 g of Pluronic F 108, 10 g of Morwet D-425, 50 g of propylene glycol, 30 g of Biopolymer prepared as described under a) and 2 g of Proxel GXL are dissolved in 470 g of buffer solution prepared as described under b).

e) Preparation of the Aqueous Emulsion Concentrate

Using the YSTRAL X 40/32 emulsifier, the aqueous phase is stirred at about 600 rpm and the oil phase is then added; the mixture is emulsified at about 5000 rpm over the course of from 3 to 4 minutes until a particle size of from 2 to 4 micrometres is obtained. Then, in order to achieve the desired viscosity, 40 g of Biopolymer prepared as described under a) are added with stirring using a magnetic stirrer (in order to obtain the gel structure of the concentrate).

On the basis of that Example, the following compositions according to the invention can also be prepared (percentages are % by weight, based on the complete formulation):

Example C1
Clodinafop-propargyl Content of 50 g/l
Oil Phase

| | |
|---|---|
| 5% | clodinafop-propargyl |
| 1.25% | cloquintocet-mexyl |
| 38% | rapeseed oil methyl ester |
| 3.7% | polystyrene |

Aqueous Phase

| | |
|---|---|
| 0.07% | xanthan gum |
| 1% | Pluronic F-108 |
| 0.2% | Proxel GXL |
| ~51% | water pH 4 (buffer [0.1 M]: 1.15% $Na_3PO_4 \cdot 12\ H_2O$, 0.91% $H_3PO_4$ (75%), 97.94% water) |

Example C2
Clodinafop-propargyl Content of 100 g/l
Oil Phase

| | |
|---|---|
| 10% | clodinafop-propargyl |
| 2.5% | cloquintocet-mexyl |
| 18% | benzoic acid methyl ester |
| 1.6% | polystyrene |

Aqueous Phase

| | |
|---|---|
| 0.2% | xanthan gum |
| 4.8% | propylene glycol |
| 2.0% | Pluronic F-108/Morwet D-425 (1:1) |
| 0.2% | Proxel GXL |
| ~60.7% | water pH 4 (buffer [0.1 M]: 1.15% $Na_3PO_4 \cdot 12\ H_2O$, 0.91% $H_3PO_4$ (75%) 97.94% water) |

Example C3
Clodinafop-propargyl Content of 100 g/l
Oil Phase

| | |
|---|---|
| 10% | clodinafop-propargyl |
| 2.5% | cloquintocet-mexyl |
| 35% | isobornyl acetate |
| 2.5% | polyvinyl acetate |

Aqueous Phase

| | |
|---|---|
| 0.1% | xanthan gum |
| 4.9% | propylene glycol |
| 2.0% | Pluronic F-108/Morwet D-425 (1:1) |
| 0.2% | Proxel GXL |
| ~43% | water pH 4 (buffer [0.1 M]: 1.15% $Na_3PO_4 \cdot 12\ H_2O$, 0.91% $H_3PO_4$ (75%), 97.94% water) |

Example C4
Clodinafop-propargyl Content of 100 g/l
Oil Phase

| | |
|---|---|
| 10% | clodinafop-propargyl |
| 2.5% | cloquintocet-mexyl |
| 34% | isobornyl acetate |
| 2.4% | polypropylene glycol |

Aqueous Phase

| | |
|---|---|
| 0.1% | xanthan gum |
| 4.8% | propylene glycol |
| 2.0% | Pluronic F-108/Morwet D-425 (1:1) |
| 0.2% | Proxel GXL |
| ~44% | water pH 4 (buffer [0.1 M]: 1.15% $Na_3PO_4.12\ H_2O$, 0.91% $H_3PO_4$ (75%), 97.94% water) |

Example C5
Clodinafop-propargyl Content of 150 g/l
Oil Phase

| | |
|---|---|
| 15% | clodinafop-propargyl |
| 3.75% | cloquintocet-mexyl |
| 45% | Exxate 700 |
| 3.3% | polyvinyl acetate |

Aqueous Phase

| | |
|---|---|
| 0.08% | xanthan gum |
| 5.0% | propylene glycol |
| 2.0% | Pluronic F-108/Morwet D-425 (1:1) |
| 0.2% | Proxel GXL |
| ~26% | water pH 4 (buffer [0.1 M]: 1.15% $Na_3PO_4.12\ H_2O$, 0.91% $H_3PO_4$ (75%), 97.94% water) |

Example C6
Clodinafop-propargyl Content of 200 g/l
Oil Phase

| | |
|---|---|
| 20% | clodinafop-propargyl |
| 5% | cloquintocet-mexyl |
| 40% | Solvesso 200 (high-aromatic-content hydrocarbon mixture) |
| 3.4% | polystyrene |

Aqueous Phase

| | |
|---|---|
| 3.7% | propylene glycol |
| 2.0% | Pluronic F-108/Morwet D-425 (1:1) |
| 0.2% | Proxel GXL |
| ~26% | water pH 4 (buffer [0.1 M]: 1.15% $Na_3PO_4.12\ H_2O$, 0.91% $H_3PO_4$ (75%), 97.94% water) |

Example C7
Clodinafop-propargyl Content of 240 g/l
Oil Phase

| | |
|---|---|
| 24% | clodinafop-propargyl |
| 6% | cloquintocet-mexyl |
| 24.6% | benzyl acetate |
| 3.2% | polypropylene glycol |

Aqueous Phase

| | |
|---|---|
| 0.05% | xanthan gum |
| 4.8% | propylene glycol |
| 2.0% | Pluronic F-108/Morwet D-425 (1:1) |
| 0.2% | Proxel GXL |
| ~35% | water pH 4 (buffer [0.1 M]: 1.15% $Na_3PO_4.12\ H_2O$, 0.91% $H_3PO_4$ (75%), 97.94% water) |

Example C8
Clodinafop-propargyl Content of 240 g/l
Oil Phase

| | |
|---|---|
| 24% | clodinafop-propargyl |
| 6% | cloquintocet-mexyl |
| 29% | acetophenone/amyl acetate (2:8) |
| 2.5% | polystyrene |

Aqueous Phase

| | |
|---|---|
| 0.03% | xanthan gum |
| 5.0% | propylene glycol |
| 2.0% | Pluronic F-108/Morwet D-425 (1:1) |
| 0.2% | Proxel GXL |
| ~31% | water pH 4 (buffer [0.1 M]: 1.15% $Na_3PO_4.12\ H_2O$, 0.91% $H_3PO_4$ (75%), 97.94% water) |

Before application, the concentrated formulations set out above are diluted with an amount of 400 litres of water per hectare.

Biological Examples

Clodinafop-propargyl is generally used on the plant or the locus thereof in rates of application of from 5 to 200 g/ha, especially from 10 to 50 g/ha, more especially from 20 to 30 g/ha.

The rates of application of cloquintocet-mexyl are generally from 2 to 100 g/ha, preferably from 2 to 50 g/ha, especially from 5 to 7.5 g/ha.

The concentration required to achieve the desired action can be determined by experimentation. It will depend on the type of action, the development stage of the cultivated plant and of the weed, as well as on the application (place, time, method), and in dependence on those parameters can vary over a wide range.

The amount of safener to be applied in relation to the herbicide is largely dependent upon the type of application. In the case of field treatment, which is effected either using a tank mixture with a combination of the safener and the herbicide or by the separate application of the safener and the herbicide, the ratio of herbicide to safener is generally from 1:1 to 10:1, preferably 4:1.

The herbicidal activity of the aqueous emulsions according to the invention is demonstrated in the following biological Examples:

Example B1
Herbicidal Action after Emergence of the Plants (Post-emergence Action)

Monocotyledonous and dicotyledonous weeds are grown under greenhouse conditions in standard soil in plastic pots. Application of the test substances is carried out when the plants are at the 3- to 6-leaf stage. Application is carried out in the form of an aqueous emulsion of the test substances in 400 litres of water per hectare. The rates of application depend on the optimum doses ascertained under field conditions and greenhouse conditions. The tests are evaluated after 20 days (% action, 100%=plant has died, 0%=no phytotoxic action).

Test plants: Alopecurus, *Lolium rigidum, Lolium multiflorum, Agrostis*.

Compositions of the Formulations Used

Composition no. C9 according to the present invention

| Ingredient: | Amount in % by weight |
|---|---|
| clodinafop-propargyl (herbicide) | 10.0 |
| cloquintocet-mexyl (safener) | 2.5 |
| benzoic acid methyl ester (solvent) | 18.0 |
| polypropylene glycol T01/60 (oil phase stabiliser) | 1.6 |
| Pluronic F-108 (surfactant) | 1.0 |
| Morwet D-425 (surfactant) | 1.0 |
| propylene glycol (anti-freeze agent) | 4.8 |
| xanthan gum (thickener) | 0.2 |
| Proxel GXL (biocide) | 0.2 |
| water buffer pH 4 (buffer [0.1 M]: 1.15% $Na_3PO_4.12\ H_2O$ 0.91% $H_3PO_4$ (75%), 97.94% water) | 60.7 |

Composition no. C10 according to the present invention

| Ingredient: | Amount in % by weight |
|---|---|
| clodinafop-propargyl (herbicide) | 10.0 |
| cloquintocet-mexyl (safener) | 2.5 |
| Exxate 700 (solvent) | 24.0 |
| polystyrene (oil phase stabiliser) | 1.9 |
| Pluronic F-108 (surfactant) | 1.0 |
| Morwet D-425 (surfactant) | 1.0 |
| propylene glycol (anti-freeze agent) | 4.7 |
| xanthan gum (thickener) | 0.2 |
| Proxel GXL (biocide) | 0.2 |
| water buffer pH 4 (buffer [0.1M]: 1.15% Na$_3$PO$_4$.12 H$_2$O 0.91% H$_3$PO$_4$ (75%), 97.94% water) | 54.5 |

Composition no. C11 according to the present invention

| Ingredient: | amount in % by weight |
|---|---|
| clodinafop-propargyl (herbicide) | 10.0 |
| cloquintocet-mexyl (safener) | 2.5 |
| Solvesso 200 (solvent) | 25.0 |
| polyglycol (o.p.s.) | 2.0 |
| Pluronic F-108 (surfactant) | 1.0 |
| Morwet D-425 (surfactant) | 1.0 |
| propylene glycol (anti-freeze agent) | 4.9 |
| xanthan gum (thickener) | 0.2 |
| Proxel GXL (biocide) | 0.2 |
| water buffer pH 4 (buffer [0.1M]: 1.15% Na$_3$PO$_4$.12 H$_2$O 0.91% H$_3$PO$_4$ (75%), 97.94% water) | 53.2 |

Emulsifiable concentrate EC 100 of clodinafop-propargyl and cloquintocet-mexyl known under the trade name CELIO®

| Ingredient: | [% by weight] |
|---|---|
| clodinafop-propargyl (herbicide) | 10.0 |
| cloquintocet-mexyl (safener) | 2.5 |
| castor oil polyglycol 36-37 (surfactant) | 8.32 |
| dodecyl-benzenesulfonic acid calcium salt, linear (surfactant) | 6.66 |
| 1-methyl-2-pyrrolidone (solvent) | 20.0 |
| soybean oil, epoxidised (dispersing agent) | 1.0 |
| high-aromatic-content hydrocarbon mixture (solvent) (Solvesso 200) | remainder |

Before application, the concentrated formulations set out above are diluted with an amount of 400 litres of water per hectare.

TABLE B1

Post-emergence action; rate of application of clodinafop-propargyl: 30 g/ha: rate of application of cloquintocet-mexyl: 7.5 g/ha:

| | Formulation no.: | | | |
|---|---|---|---|---|
| Test plant: | C9 | C10 | C11 | EC 100 |
| Alopecurus | 95 | 90 | 90 | 80 |
| Lolium rigidum | 90 | 90 | 90 | 80 |
| Lolium multiflorum | 95 | 95 | 90 | 80 |
| Agrostis | 60 | 50 | 40 | 30 |

Table B1 shows that, in this test, the compositions according to the invention have surprisingly improved herbicidal action on the tested weeds compared to the known emulsifiable concentrate (EC 100). Especially in the case of Alopecurus and Lolium, it was possible for the herbicidal action to be increased almost to complete destruction of the weed (95% herbicidal action).

In addition to the surprisingly improved herbicidal activity of clodinafop-propargyl, the compositions according to the invention have the following advantageous properties:

stable emulsion droplets are formed which, even when stored for a relatively long period, exhibit no appreciable particle size growth and no phase separation;

the clodinafop-propargyl and the cloquintocet-mexyl, which is optionally present in addition, have a high degree of chemical stability, resulting from appropriate selection of the solvent and pH buffer system;

a high degree of stability in the cold, and therefore good suitability for storage even at low temperatures;

no crystallisation of the herbicide or safener occurs in the event of temperature changes; and no phase separation occurs in the event of freeze/thaw cycles.

What is claimed is:

1. A herbicidal composition in the form of an aqueous emulsion which comprises
   a), as organic phase, a solution of a herbicidally effective amount of the compound 2-(4-(5-chloro-3-fluoro-2-pyridyloxy)-phenoxy-propionic acid propargyl ester in a hydrophobic solvent and a substantially water-insoluble and hydrolysis-stable oil phase stabiliser and
   b), as aqueous phase, a solution of a pH buffer and at least one surface-active compound and/or dispersing agent in water.

2. A composition according to claim 1, which comprises an amount, effective for antagonism of the herbicide, of 2-(5-chloroquinolin-8-yloxy)-1-methylhexyl ester, its free acid or a salt thereof of formula

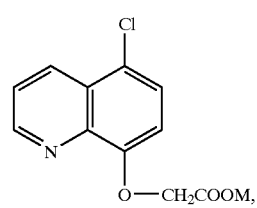

(I)

wherein M is a mono-, bi- or tri-valent metal, ammonium, N(R)$_4$ or HN(R)$_3$, wherein the substituents R are identical to or different from one another and are C$_1$–C$_{16}$alkyl or C$_1$–C$_{16}$-hydroxyalkyl, or M is S(R$_1$)$_3$ or P(R$_1$)$_4$, wherein the substituents R$_1$ are identical to or different from one another and are C$_1$–C$_{20}$alkyl, C$_2$–C$_{20}$alkenyl, C$_2$–C$_{20}$alkynyl, aryl substituted by C$_1$–C$_{20}$alkyl, C$_2$–C$_{20}$alkenyl or by C$_2$–C$_{20}$alkynyl or heteroaryl substituted by C$_1$–C$_{20}$alkyl, C$_2$–C$_{20}$alkenyl or by C$_2$–C$_{20}$alkynyl, or 2 substituents R$_1$ together with the sulfur or phosphorus atom to which they are bonded form a 5- or 6-membered ring.

3. A composition according to claim 1, which comprises an amount, effective for antagonism of the herbicide, of 2-(5-chloroquinolin-8-yloxy)-1-methylhexyl ester.

4. A method of controlling undesired plant growth, which comprises applying a herbicidally effective amount of a composition according to claim 1 to the plants or to the locus thereof.

* * * * *